United States Patent
Loughner et al.

(10) Patent No.: US 8,071,506 B2
(45) Date of Patent: Dec. 6, 2011

(54) SYNERGISTIC HERBICIDAL COMPOSITION CONTAINING FLORASULAM FOR WEED CONTROL IN TURF

(75) Inventors: Daniel L. Loughner, Princeton, NJ (US); Randy L. Smith, Westfield, IN (US); Michael W. Melichar, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 119 days.

(21) Appl. No.: 12/759,863

(22) Filed: Apr. 14, 2010

(65) Prior Publication Data

US 2010/0267559 A1 Oct. 21, 2010

Related U.S. Application Data

(60) Provisional application No. 61/169,454, filed on Apr. 15, 2009.

(51) Int. Cl.
| | |
|---|---|
| *A01N 63/00* | (2006.01) |
| *A01N 43/60* | (2006.01) |
| *A01N 33/18* | (2006.01) |
| *A01N 39/02* | (2006.01) |
| *A01N 43/90* | (2006.01) |
| *A01N 43/40* | (2006.01) |

(52) U.S. Cl. ........ 504/118; 504/136; 504/145; 504/250; 504/347; 514/188; 514/259.31

(58) Field of Classification Search .................. 504/136, 504/118, 145, 250, 347
See application file for complete search history.

(56) References Cited

FOREIGN PATENT DOCUMENTS

| | | |
|---|---|---|
| EP | 0 512 737 A1 | 11/1992 |
| EP | 2 095 712 A1 | 9/2009 |
| WO | WO 2006/065094 A1 | 6/2006 |
| WO | PCT/US2010/031000 | 4/2010 |

OTHER PUBLICATIONS

Anonymous: "Penoxsulam and its Use as a Herbicide in Mixtures for use in Rice, Wheat, Barley, Oats, Sorghum, Corn, Maize, IVM, Rangeland, Pastures, Grasslands, Fallowland, Turf and Aquatics" IP.COM Journal, IP.COM Inc., West Henrietta, NY, US, Mar. 30, 2005, XP013024048 ISSN: 1533-0001.

*Primary Examiner* — Johann R. Richter
*Assistant Examiner* — Andriae M Holt
(74) *Attorney, Agent, or Firm* — Craig E. Mixan

(57) ABSTRACT

An herbicidal composition containing (a) florasulam and (b) at least one preemergent annual grass herbicide selected from the group consisting of dithiopyr and pendimethalin provides synergistic control of selected weeds in turf.

5 Claims, No Drawings

SYNERGISTIC HERBICIDAL COMPOSITION CONTAINING FLORASULAM FOR WEED CONTROL IN TURF

This application claims the benefit of U.S. Provisional Application Ser. No. 61/169,454 filed on Apr. 15, 2009. This invention concerns a synergistic herbicidal composition containing (a) florasulam and (b) at least one preemergent annual grass herbicide selected from the group consisting of dithiopyr and pendimethalin.

FIELD OF THE INVENTION

Background of the Invention

The search for compounds which have a combination of excellent herbicidal activity towards target weeds and low toxicity towards non-target plants is a continuing one because of factors such as the desire for compounds exhibiting greater activity, better selectivity, lower undesirable environmental impact, lack of phytotoxicity to the locus of application, lower production and market cost and higher effectiveness against weeds resistant to known herbicides. In particular, there exists a need for effective control of broadleaf weeds in turfgrass. Commercial herbicides, for example, 2,4-D, mecoprop-P (MCPP-p), clopyralid, triclopyr and methylarsonic acid, have serious deficiencies such as requiring a high application rate to be effective, possessing less than desirable environmental profiles, having too great or too poor soil mobility and/or being toxic to non-target plants and or the turfgrass species.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462, "'synergism' [is] an interaction of two or more factors such that the effect when combined is greater than the predicted effect based on the response to each factor applied separately." The present invention is based on the discovery that certain turf herbicides and florasulam, already known individually for their herbicidal efficacy, display a synergistic effect when applied in combination.

The herbicidal compounds forming the synergistic composition of this invention are independently known in the art for their effects on plant growth.

SUMMARY OF THE INVENTION

The present invention concerns a synergistic herbicidal mixture comprising an herbicidally effective amount of (a) florasulam and (b) at least one preemergent annual grass herbicide selected from the group consisting of dithiopyr and pendimethalin. The present invention also concerns herbicidal compositions for controlling the growth of undesirable vegetation, particularly in turf. The present invention also concerns methods of controlling the growth of undesirable vegetation in turf which comprises contacting the undesirable vegetation or the locus thereof with or applying to the soil or water to prevent the emergence or growth of vegetation an herbicidally effective amount of the herbicidal mixture. The present invention also concerns methods of controlling the growth of undesirable broadleaf vegetation in turf with a preemergent application of florasulam that coincides with the application of preemergent grass herbicide. The synergistic mixtures of the present invention also demonstrate greater than expected control of certain weed species when used in conjunction with other turf herbicides including 2,4-D, MCPP-p, dicamba or mixtures thereof.

The species spectra of the compounds of the synergistic mixture, i.e., the weed species which the respective compounds control, are broad and highly complimentary. For example, it has been surprisingly found that a combination of florasulam and at least one preemergent annual grass herbicide selected from the group consisting of dithiopyr and pendimethalin exhibits a synergistic action in the control of white clover (*Trifolium repens*; TRFRE), dandelion (*Taraxacum officinale*; TAROF), crabgrass (*Digitaria* sp.; DIGSS) and buckhorn plantain (*Plantago lanceolata*; PLALA) in turf applications at rates lower than the rates of the individual compounds.

DETAILED DESCRIPTION OF THE INVENTION

Florasulam is the common name for N-(2,6-difluorophenyl)-8-fluoro-5-methoxyl[1,2,4]triazolo[1,5-c]pyrimidine-2-sulfonamide. Its herbicidal activity is described in *The Pesticide Manual*, Fourteenth Edition, 2006. Florasulam provides postemergent control of broadleaf weeds and cruciferae in cereals and maize.

Dithiopyr is the common name for S,S'-dimethyl 2-(difluoromethyl)-4-(2-methylpropyl)-6-(trifluoromethyl)-3,5-pyridinedicarbothioate. Its herbicidal activity is described in *The Pesticide Manual*, Fourteenth Edition, 2006. Dithiopyr is used for preemergence and early postemergence control of annual grass weeds and some broadleaf weeds in turf.

Pendimethalin is the common name for N-(1-ethylpropyl)-3,4-dimethyl-2,6-dinitrobenzenamine. Its herbicidal activity is described in *The Pesticide Manual*, Fourteenth Edition, 2006. Pendimethalin controls most annual grass weeds and many annual broadleaf weeds.

Dicamba is the common name for 3,6-dichloro-2-methoxybenzoic acid. Its herbicidal activity is described in *The Pesticide Manual*, Fourteenth Edition, 2006. Dicamba controls annual and perennial broadleaf weeds.

2,4-D is the common name for (2,4-dichlorophenoxy)acetic acid. Its herbicidal activity is described in *The Pesticide Manual*, Fourteenth Edition, 2006. 2,4-D provides postemergent control of annual and perennial broadleaf weeds.

MCPP-p or mecoprop-p is the common name for (R)-2-(4-chloro-2-methylphenoxy)propanoic acid. Its herbicidal activity is described in *The Pesticide Manual*, Fourteenth Edition, 2006. MCPP-p provides postemergent control of broadleaf weeds.

Postemergent herbicide applications are typically timed for peak dandelion bloom in late spring approximately six to eight weeks after preemergent herbicide applications targeting annual grassy weeds, such as crabgrass, goosegrass and foxtail. Surprisingly, florasulam, which is recommended for postemergent applications, effectively controls key broadleaf weeds such as white clover and dandelion when applications are made at the preemergent herbicide application timing. In addition, when combined with a preemergent annual grass herbicide, namely dithiopyr or pendimethalin, broadleaf weed control improves demonstrating synergism.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation and the like. The terms plants and vegetation include germinant seeds, emerging seedlings, plants emerging from vegetative propagules and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type and the like, as well as the amount of chemical applied. These and other factors can be adjusted as is known in the art to promote non-selective or selective herbicidal action.

In the composition of this invention, the weight ratio of florasulam to dithiopyr at which the herbicidal effect is synergistic lies within the range of between about 1:10 and about 1:170. The weight ratio of florasulam to pendimethalin at which the herbicidal effect is synergistic lies within the range of between about 1:75 and about 1:1000.

The rate at which the synergistic composition is applied will depend upon the particular type of weed to be controlled, the degree of control required and the timing and method of application. In general, the composition of the invention can be applied at an application rate of between about 150 grams per hectare (g/ha) and about 3400 g/ha based on the total amount of active ingredients in the composition. Dithiopyr is applied at a rate between about 140 g/ha and about 575 g/ha and florasulam is applied at a rate between about 3 g/ha and about 20 g/ha. Pendimethalin is applied at a rate between about 1150 g/ha and about 3380 g/ha and florasulam is applied at a rate between about 3 g/ha and about 20 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic mixture include 2,4-D, 2,4-DP, 2,4-DB, acetochlor, acifluorofen, aclonifen, alachlor, amiprofos-methyl, aminopyralid, ametryn, aminotriazole, ammonium thiocyanate, asulam, atrazine, azimsulfuron, benefin, benfluralin, benfuresate, bensulide, bentazon, bethrodine, bialaphos, bifenox, bispyribac-sodium, bromacil, bromoxynil, butafenacil, butamifos, butralin, cafenstrole, carbetamide, carfentrazone, carfentrazone-ethyl, clethodim, cloransulam, chlorphthalim, chlorpropham, chlorsulfuron, chlorflurenol, chlorthal-dimethyl, chlorthiamid, cinmethylin, cinosulfuron, clopyralid, clomazone, cumyluron, cyanazine, cyclosulfamuron, cycloxydim, DCPA, dicamba, dichlobenil, diclofop, dichlorprop-P, diclosulam, diflufenican, diflufenzopyr, diquat, diuron, DSMA, endothal-disodium, EPTC, ET-751, ethofumesate, ethoxysulfuron, flazasulfuron, flazasulfuron, flucetosulfuron, flumetsulam, foramsulfuron, fluazifop, fluazifop-P-butyl, flucetosulfuron, flufenacet, flumioxazin, flupoxam, flupyrsulfuron, fluoroxypyr, glufosinate, glufosinate-ammonium, glyphosate, haloxyfop-methyl, halosulfuron, hexazinone, imazaquin-ammonium, imazethapyr, imazosulfuron, indanofan, iodosulfuron, ioxynil, isoproturon, iodosulfuron, isoxaben, isoxaflutole, imazamox, imazapyr, imazaquin, imazapic, kerbutilate, KIH-485, lenacil, MCPA, mecoprop-P, MCPP, MSMA, mesosulfuron, mesotrione, methyl daimuron, metolachlor, metribuzin, metsulfuron, metsulfuron-methyl, napropamide, nicosulfuron, norflurazon, orthobencarb, orthosulfamuron, oryzalin, oxadiargyl, oxadiazon, oxaziclomefone, oxyfluorfen, paraquat, pebulate, picolinafen, picloram, pinoxaden, primisulfuron, prodiamine, prosulfuron, profluazol, propoxycarbazone, propyzamide, prosulfocarb, prodiamine, pyrazone, pyrazosulfuron-ethyl, pyributicarb, pyrithiobac, pyraflufen-ethyl, pyrimisulfan, pyroxsulam, quinoclamine, quinclorac, quizalofop-ethyl-D, rimsulfuron, sethoxydim, siduron, simazine, sulfentrazone, sulfosate, sulfosulfuron, sulfometuron, tebuthiuron, terbacil, thenylchlor, thiazopyr, thifensulfuron, topramezone, tralkoxydim, triclopyr, trifluralin, trifloxysulfuron-sodium, tritosulfuron and triaziflam. It is generally preferred to apply the synergistic mixture and other complementary herbicides at the same time, either as a combination formulation or as a tank mix. When applying in this way, synergistic responses have been observed specific to species and mixture, particularly when the synergistic mixtures of florasulam with dithiopyr or pendimethalin are used in conjunction with 2,4-D, MCPP-p, dicamba or mixtures thereof.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to turf, particularly at the concentrations employed in applying the compositions for selective weed control in turf, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, wettable powders or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, solid fertilizers and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents and the like. The compositions may also contain other compatible components, for example, other herbicides, plant growth regulators, fungicides, insecticides and the like and can be formulated with liquid fertilizers or solid, particulate fertilizer carriers such as ammonium nitrate, urea and the like that are used to deliver nutrients to turfgrass.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground sprayers, granule applicators, and by other conventional means known to those skilled in the art.

The following examples illustrate the present invention.

EXAMPLES

Field studies were conducted in established turfgrass sites containing a natural population of target broadleaf weeds. Replicated trials, containing a minimum of three replications and having individual plots ranging in size from 25 to 50 ft. sq, were initiated in the early spring with turf and weeds still in dormancy or just beginning active growth. Studies containing two components (florasulam and dithiopyr or pendimethalin) were timed to coincide with typical preemergent crabgrass (*Digitaria* sp.) timing at the study location. Studies containing three components (florasulam, dithiopyr or pendimethalin, Trimec (2,4-D+dicamba+MCPP-p) or Scotts Plus 2 (2,4-D+MCPP-p) were timed as previous for the florasulam and dithiopyr or pendimethalin components followed by an application of Trimec or Scotts Plus 2 at peak dandelion bloom which occurs approximately six weeks after a typical preemergent application. Granule treatments were uniformly applied to individual plots using a common hand-shaker or shaker table method. Liquid applications were applied with a $CO_2$ backpack sprayer calibrated to deliver 40 to 100 GPA at 40 to 60 PSI. Applications were generally made in the early morning when dew was present. Natural rainfall and supplemental irrigation were used to maintain healthy turf and active weed growth throughout the study period. Weed control evaluations were made by visually assessing percent weed cover of each weed species in each plot at the initiation of the study and at each evaluation interval, converting to percent control using the following formula:

$$(1-(B/A))*100$$

A=percent weed cover at study initiation
B=percent weed at a specific evaluation interval after application Using this method, control ranges occur between 0 and 100 percent where 0 corresponds to no control and 100 corresponds to complete kill. Percent cover of each weed species was made at approximately 2, 4 and 8 weeks after treatment.

The following equation was used to calculate the expected activity of mixtures containing two active ingredients, A and B:

$$Expected=A+B-(A\times B/100)$$

A=observed efficacy of active component A at the same concentration as used in the mixture.
B=observed efficacy of active component B at the same concentration as used in the mixture.

The following equation was used to calculate the expected activity of mixtures containing three active ingredients, A and B and C:

$$Expected=A+B+C-((A\times B)+(A\times C)+(B\times C)/100)+(A\times B\times C/10,000)$$

A=observed efficacy of active component A at the same concentration as used in the mixture.
B=observed efficacy of active component B at the same concentration as used in the mixture.
C=observed efficacy of active component C at the same concentration as used in the mixture.

Treatments evaluated, application rate employed, weed species evaluated and results are presented in the following Tables 1-13.

TABLE 1

Synergistic Activity of Herbicidal Compositions on White Clover (TRFRE) 62 DAT in Turf

| g ai/ha | | | | |
| --- | --- | --- | --- | --- |
| Dithiopyr GR | Florasulam GR | Observed | Expected | Observed vs. Expected |
| 575 | — | 0 | — | — |
| — | 15 | 0 | — | — |
| 575 | 15 | 39 | 0 | 39 |

TABLE 2

Synergistic Activity of Herbicidal Compositions on Dandelion (TAROF) 56 DAT in Turf

| g ai/ha | | | | |
| --- | --- | --- | --- | --- |
| Dithiopyr GR | Florasulam GR | Observed | Expected | Observed vs. Expected |
| 575 | — | 29 | — | — |
| — | 15 | 0 | — | — |
| 575 | 15 | 74 | 29 | 45 |

TABLE 3

Synergistic Activity of Herbicidal Compositions on Dandelion (TAROF) 36 DAT in Turf

| g ai/ha | | | | |
|---|---|---|---|---|
| Dithiopyr GR | Florasulam GR | Observed | Expected | Observed vs. Expected |
| 575 | — | 0 | — | — |
| — | 15 | 20 | — | — |
| 575 | 15 | 49 | 20 | 29 |

TABLE 4

Synergistic Activity of Herbicidal Compositions on Dandelion (TAROF) 91 DAT in Turf

| g ai/ha | | | | |
|---|---|---|---|---|
| Dithiopyr GR | Florasulam GR | Observed | Expected | Observed vs. Expected |
| 575 | — | 19 | — | — |
| — | 15 | 18 | — | — |
| 575 | 15 | 57 | 33.6 | 23.4 |

TABLE 5

Synergistic Activity of Herbicidal Compositions on White Clover (TRFRE) 36 DAT in Turf

| g ai/ha | | | | |
|---|---|---|---|---|
| Dithiopyr GR | Florasulam GR | Observed | Expected | Observed vs. Expected |
| 575 | — | 0 | — | — |
| — | 15 | 73 | — | — |
| 575 | 15 | 94 | 73 | 21 |

TABLE 6

Synergistic Activity of Herbicidal Compositions on Dandelion (TAROF) 58 DAT in Turf

| g ai/ha | | | | |
|---|---|---|---|---|
| Dithiopyr 2EW | Florasulam SC | Observed | Expected | Observed vs. Expected |
| 575 | — | 21.7 | — | — |
| — | 15 | 70 | — | — |
| 575 | 15 | 95 | 76.5 | 18.5 |

TABLE 7

Synergistic Activity of Herbicidal Compositions on White Clover (TRFRE) 28 DAT in Turf

| g ai/ha | | | | |
|---|---|---|---|---|
| Dithiopyr GR | Florasulam GR | Observed | Expected | Observed vs. Expected |
| 575 | — | 0 | — | — |
| — | 15 | 86.8 | — | — |
| 575 | 15 | 97.3 | 86.8 | 10.5 |

TABLE 8

Synergistic Activity of Herbicidal Compositions on Buckhorn Plantain (PLALA) 27 DAT in Turf

| g ai/ha | | | | |
|---|---|---|---|---|
| Pendimethalin GR | Florasulam GR | Observed | Expected | Observed vs. Expected |
| 2300 | — | 0 | — | — |
| — | 15 | 26.7 | — | — |
| 2300 | 15 | 53.3 | 26.7 | 26.6 |

TABLE 9

Synergistic Activity of Herbicidal Compositions on Dandelion (TAROF) 64 DAT in Turf

| g ai/ha | | Pt/A | | | Observed |
|---|---|---|---|---|---|
| Dithiopyr GR | Florasulam GR | Trimec EC[1] | Observed | Expected | vs. Expected |
| 575 | — | — | 0 | — | — |
| — | 15 | — | 30 | — | — |
| — | — | 4 | 46.3 | — | — |
| 575 | 15 | 4 | 98 | 62.4 | 35.6 |

[1]Trimec is a liquid mixture of 2,4-D + dicamba + MCPP-p

TABLE 10

Synergistic Activity of Herbicidal Compositions on Dandelion (TAROF) 59 DAT in Turf

| g ai/ha | | Pt/A | | | Observed |
|---|---|---|---|---|---|
| Dithiopyr GR | Florasulam GR | Trimec EC[1] | Observed | Expected | vs. Expected |
| 575 | — | — | 27 | — | — |
| — | 15 | — | 0 | — | — |
| — | — | 4 | 33 | — | — |
| 575 | 15 | 4 | 67 | 51.1 | 15.9 |

[1]Trimec is a liquid mixture of 2,4-D + dicamba + MCPP-p

TABLE 11

Synergistic Activity of Herbicidal Compositions on Dandelion (TAROF) 57 DAT in Turf

| g ai/ha | | Pt/A | | | Observed |
|---|---|---|---|---|---|
| Dithiopyr GR | Florasulam GR | Trimec EC[1] | Observed | Expected | vs. Expected |
| 575 | — | — | 21 | — | — |
| — | 15 | — | 31 | — | — |
| — | — | 4 | 72 | — | — |
| 575 | 15 | 4 | 98 | 84.7 | 13.3 |

[1]Trimec is a liquid mixture of 2,4-D + dicamba + MCPP-p

TABLE 12

Synergistic Activity of Herbicidal Compositions on White Clover (TRFRE) 55 DAT in Turf

| g ai/ha | | Lb/A | | | Observed |
|---|---|---|---|---|---|
| Pendimethalin GR | Florasulam GR | Scotts Plus 2[1] | Observed | Expected | vs. Expected |
| 2300 | — | — | 0 | — | — |
| — | 15 | — | 62.5 | — | — |

TABLE 12-continued

Synergistic Activity of Herbicidal Compositions on White Clover (TRFRE) 55 DAT in Turf

| g ai/ha | | Lb/A | | | Observed |
|---|---|---|---|---|---|
| Pendimethalin GR | Florasulam GR | Scotts Plus 2[1] | Observed | Expected | vs. Expected |
| — | — | 125 | 0 | — | — |
| 2300 | 15 | 125 | 92.7 | 62.5 | 30.2 |

[1]Scotts Plus 2 is a granule mixture of 2,4-D + MCPP-p

TABLE 13

Synergistic Activity of Herbicidal Compositions on Dandelion (TAROF) 60 DAT in Turf

| g ai/ha | | Lb/A | | | Observed |
|---|---|---|---|---|---|
| Pendimethalin GR | Florasulam GR | Scotts Plus 2[1] | Observed | Expected | vs. Expected |
| 2300 | — | — | 21 | — | — |
| — | 15 | — | 20.6 | — | — |
| — | — | 125 | 27 | — | — |
| 2300 | 15 | 125 | 84.3 | 54.2 | 30.1 |

[1]Scotts Plus 2 is a granule mixture of 2,4-D + dicamba + MCPP-p

What is claimed is:

1. A synergistic herbicidal mixture comprising an herbicidally effective amount of (a) florasulam and (b) at least one preemergent annual grass herbicide selected from the group consisting of dithiopyr and pendimethalin, wherein the weight ratio of florasulam to dithiopyr is between 1:10 and 1:38 and the weight ratio of florasulam to pendimethalin is between 1:75 and 1:153.

2. The mixture of claim 1 in which the synergistic mixture of florasulam and the preemergent annual grass herbicide is used in conjunction with 2,4-D, MCPP-p, dicamba or mixtures thereof.

3. An herbicidal composition comprising an herbicidally effective amount of the herbicidal mixture of claim 1 and an agriculturally acceptable adjuvant or carrier.

4. A method of controlling undesirable vegetation in turf which comprises contacting the undesirable vegetation or the locus thereof with or applying to the soil or water to prevent the emergence or growth of the undesirable vegetation an herbicidally effective amount of the herbicidal mixture of claim 1.

5. The method of claim 4 for controlling undesirable broadleaf vegetation in turf which comprises contacting the locus thereof with or applying to the soil to prevent the emergence or growth of the undesirable broadleaf vegetation a preemergent application of florasulam that coincides with the application of the preemergent grass herbicide.

* * * * *